United States Patent [19]
Han et al.

[11] Patent Number: 6,114,552
[45] Date of Patent: Sep. 5, 2000

[54] HETEROGENEOUS EPOXIDATION CATALYST

[75] Inventors: Yuan-Zhang Han; Edrick Morales; Robert G. Gastinger, all of West Chester; Kevin M. Carroll, Havertown, all of Pa.

[73] Assignee: Arco Chemical Technology, L.P., Greenville, Del.

[21] Appl. No.: 09/407,489

[22] Filed: Sep. 28, 1999

[51] Int. Cl.⁷ .................................................. C07D 301/19
[52] U.S. Cl. .............................................................. 549/529
[58] Field of Search ............................................. 549/529

[56] References Cited

U.S. PATENT DOCUMENTS

| | | | |
|---|---|---|---|
| 3,829,392 | 8/1974 | Wulff | 252/430 |
| 3,923,843 | 12/1975 | Wulff | 260/348.5 L |
| 4,021,454 | 5/1977 | Wulff et al. | 260/348.5 L |

FOREIGN PATENT DOCUMENTS

| | | |
|---|---|---|
| 0 323 663 | 7/1989 | European Pat. Off. . |
| 0 345 856 | 12/1989 | European Pat. Off. . |
| 1332527 | 10/1973 | United Kingdom . |
| WO 98/50374 | 11/1998 | WIPO . |

OTHER PUBLICATIONS

Edler et al., *J. Chem. Soc., Chem. Comm.* (1995), pp. 155–159 Room–temperature Formation of Molecular Sieve MCM–41.

Tanev, et al., *Nature* (1994) V. 368, pp. 321–323.

Maschmeyer, et al., *Nature* (1995) V. 378, pp. 159–162.

*Primary Examiner*—Ba K. Trinh
*Attorney, Agent, or Firm*—Kevin M. Carroll

[57] ABSTRACT

Highly active and selective epoxidation catalysts are prepared by combining high surface area silica support or the like, having surface area greater than 1100 $m^2/g$, with a titanium source. The titanium source is a non-oxygenated hydrocarbon solution of a titanium halide or a vapor stream of titanium tetrachloride. The impregnated support it then calcined at an elevated temperature (preferably, in a substantially oxygen-free atmosphere), and, optionally, reacted with water and/or silylated. The resulting materials are highly active heterogeneous epoxidation catalysts for the reaction of olefins to with organic hydroperoxides.

13 Claims, No Drawings

HETEROGENEOUS EPOXIDATION CATALYST

FIELD OF THE INVENTION

This invention relates to a method of producing an improved titanium-containing catalyst and its use in an epoxidation process. The catalyst is obtained by impregnating a high surface area siliceous solid with a titanium halide in a hydrocarbon solvent, or a vapor stream of titanium tetrachloride, followed by calcination. The catalyst is highly active for olefin epoxidation.

BACKGROUND OF THE INVENTION

Many different methods for the preparation of epoxides have been developed. One such method involves the liquid phase epoxidation of an olefin with an organic hydroperoxide in the presence of a solubilized transition metal catalyst. Although highly active and selective for olefin epoxidation, soluble catalysts must be recovered or recycled after use to avoid loss to a waste stream. However, it can be very expensive to recover the soluble catalysts after use. In addition, recycle decreases catalyst productivity by also recycling certain heavy substances such as acids and polymers that tend to accumulate along with catalyst in the heavy bottoms stream. The recycled heavies' stream decreases epoxide selectivity or olefin conversion.

Heterogeneous (insoluble) catalysts have been developed to avoid homogeneous catalyst disadvantages. U.S. Pat. No. 4,367,342 discloses an olefin epoxidation process in the presence of an insoluble catalyst comprised of an inorganic oxygen compound of titanium. Unfortunately, the disclosed catalysts have less than optimum activity and selectivity. British Pat. No. 1,332,527 teaches a process for preparing an improved titania-silica catalyst characterized by impregnating an inorganic siliceous solid with a titanium compound in an oxygen-substituted hydrocarbon solvent, removing the solvent, and calcining the impregnated solid. Suitable solvents are limited to oxa and/or oxo-substituted hydrocarbons that are liquid at ambient conditions including alcohols, ketones, ethers, and esters. According to this patent, impregnation in an oxygen-substituted hydrocarbon solvent produced catalysts with improved properties compared to similar catalysts prepared by other methods. The alleged reason is that such catalysts have a more uniform, non-agglomerated content of titanium dioxide.

A later-filed patent application (EP 345,856) discloses the preparation of epoxidation catalysts that are alleged to be more active than the analogous catalysts obtained by previously known procedures. EP 345,856 teaches impregnation of silica with a gaseous stream of titanium tetrachloride, followed by calcination, hydrolysis, and, optionally, silylation. In a comparative example, a catalyst prepared by silica impregnated with a solution of tetra isopropyl ortho-titanate, complexed with acetyl acetone in isopropanol solvent, was found to be 4.5 times less active than the catalyst prepared by vapor phase impregnation with titanium tetrachloride. Additionally, PCT Int. Appl. WO 98/50374 discloses a catalyst prepared by a liquid phase impregnation process with a non-oxygen containing solvent. The catalyst prepared by this method has activity similar to that produced by the method of EP 345,856. Although WO 98/50374 discloses that higher surface area siliceous solids can incorporate more titanium, it does not disclose any benefits with higher surface area solids.

New methods to produce heterogeneous catalysts for olefin epoxidation have focussed on the use of high surface area, mesoporous supports such as MCM-41 and MCM-48. The methods include direct synthesis in which titanium is incorporated into the framework of the support (see Tanev, et. al., *Nature* (1994) V. 368, 321) and a grafting technique in which titanocene dichloride is grafted onto a mesoporous silica (see Maschmeyer, et. al., *Nature* (1995) V. 378, 159). Titanocene dichloride is taught to be superior to titanium tetrachloride or titanium isopropoxide due to lesser tendency to form unwanted oligomeric titanium-oxo species.

We have discovered an effective, convenient method of producing catalyst compositions having high epoxidation activity (and selectivity). These new catalyst compositions are significantly more active than catalysts obtained by techniques taught in EP 345,856, WO 98/50374, or by Maschmeyer, et. al.

SUMMARY OF THE INVENTION

The invention is an olefin epoxidation process comprising contacting an organic hydroperoxide with an olefin in the presence of a catalyst. The catalyst is produced by the method comprising: (a) impregnating a high surface area inorganic siliceous solid having surface area greater than 1100 $m^2/g$ with a titanium source; (b) calcining the impregnated solid; and (c) optionally, heating the catalyst in the presence of water. The titanium source can be either a solution of a titanium halide in a non-oxygenated hydrocarbon solvent or a vapor stream of titanium tetrachloride. Optionally, the catalyst preparation method comprises the additional step of treating the catalyst with a silylating agent.

We surprisingly found that catalysts produced by the impregnation of high surface area siliceous solids with titanium halides gave higher activity in olefin epoxidation compared to known catalyst preparation methods.

DETAILED DESCRIPTION OF THE INVENTION

The epoxidation process of the invention utilizes a titanium-containing heterogeneous catalyst that has unexpectedly been found to give superior epoxidation performance compared to materials made using other impregnation methods. In one embodiment of the invention, the catalyst preparation method is characterized by impregnating a high surface area inorganic siliceous solid, having surface area greater than 1100 $m^2/g$, with a solution of titanium halide in a non-oxygenated hydrocarbon solvent.

Suitable solvents for this purpose are those hydrocarbons that do not contain oxygen atoms, are liquid at ambient temperatures, and are capable of solubilizing the titanium halide. Generally speaking, it will be desirable to select hydrocarbon solvents wherein titanium halide concentrations of at least 0.5 percent by weight at 25° C. can be achieved. The hydrocarbon solvent should preferably be relatively volatile so that it may be readily removed from the inorganic siliceous solid following impregnation. Solvents having normal boiling points of from 25° C. to 150° C. thus may advantageously be utilized. Particularly preferred classes of hydrocarbons include $C_5$–$C_{12}$ aliphatic hydrocarbons (straight chain, branched, or cyclic), $C_6$–$C_{12}$ aromatic hydrocarbons (including alkyl-substituted aromatic hydrocarbons), $C_1$–$C_{10}$ halogenated aliphatic hydrocarbons, and $C_6$–$C_{10}$ halogenated aromatic hydrocarbons. Most preferably, the solvent does not contain elements other than carbon, hydrogen, and (optionally) halogen. If halogen is present in the solvent, it is preferably chloride.

Mixtures of non-oxygenated hydrocarbons may be used, if so desired. Preferably, the solvent used for impregnation purposes is essentially free of water (i.e., anhydrous). While oxygen-containing hydrocarbons such as alcohols, ethers, esters, ketones and the like could be present in admixture with the required non-oxygenated hydrocarbon, in one desirable embodiment of the invention only non-oxygenated hydrocarbon is present as a solvent during impregnation. Examples of suitable hydrocarbon solvents include n-hexane, n-heptane, cyclopentane, methyl pentanes, methyl cyclohexane, dimethyl hexanes, toluene, xylenes, methylene chloride, chloroform, dichloroethanes, chlorobenzene, benzyl chloride, and the like.

Unlike the procedure described in Example I of U.S. Pat. No. 4,021,454, wherein water is added to a mixture of titanium tetrachloride and silica in n-heptane, the process of this invention in preferred embodiments is characterized by the substantial exclusion of water until at least after impregnation is completed and preferably until after calcination. "Substantial exclusion" in the context of this invention means that water is not deliberately added or introduced or, if deliberately added or introduced, is removed prior to introduction of titanium halide. The use of reagents and starting materials having water present at the trace levels normally and customarily found in such substances when sold on a commercial scale is within the scope of the present invention. Preferably, less than 500 ppm water (more preferably, less than 100 ppm water) is present in the non-oxygenated hydrocarbon.

Suitable titanium halides include tri- and tetra-substituted titanium complexes that have from one to four halide substituents with the remainder of the substituents, if any, being alkoxide or amino groups. Suitable titanium halides include titanium tetrachloride, titanium tetrafluoride, titanium tetrabromide, titanium tetraiodide, titanium trichloride, as well as the mixed halides of Ti(III) or Ti(IV) titanium halides, diisopropoxytitanium dichloride, bis (diethylamino)titanium dichloride, and the like. Preferably, all the substituents attached to titanium are halide. Most preferably, the titanium halide is titanium tetrachloride.

While the concentration of titanium halide in the hydrocarbon solvent is not critical, the titanium halide concentration will typically be in the range of from 0.01 moles/liter to 1.0 moles/liter. The concentration of the titanium halide in the hydrocarbon solvent and the amount of solution used is desirably adjusted to provide a titanium content in the final catalyst of from 0.1 to 15 percent by weight (calculated as Ti based on the total weight of the catalyst). Multiple impregnations, with or without intervening drying and/or calcination, may be used to achieve the desired titanium content.

Suitable inorganic siliceous solids for purpose of this invention are solid materials that contain a major proportion of silica (silicon dioxide) and have a specific surface area of at least 1100 m$^2$/g, and preferably the average specific surface area is from 1100 m$^2$/g to 2000 m$^2$/g. The inorganic siliceous solids are porous, in that they have numerous pores, voids, or interstices throughout their structures.

Synthetic inorganic oxide materials containing a major proportion of silica comprise another class of inorganic siliceous solids. Such materials are known as refractory oxides and includes silica-alumina, silica-magnesia, silica-zirconia, silica-alumina-boric and silica-alumina-magnesia. Molecular sieves, particularly large pore or mesoporous molecular sieves such as MCM-41, MCM-48 and M41S, may also be utilized as the inorganic siliceous solid.

Preferred inorganic siliceous solids are the mesoporous molecular sieves such as MCM-41, MCM-48 and M41S. Particularly preferred is MCM-41.

It is highly desirable to dry the inorganic siliceous solid prior to impregnation. Drying may be accomplished, for example, by heating the inorganic siliceous solid for several hours at a temperature of 100° C. to 700° C., preferably at least 200° C. Generally speaking, there is no need to employ temperatures in excess of 700° C. in order to attain a sufficient degree of dryness. Vacuum or a flowing stream of a dry gas such as nitrogen may be applied to accelerate the drying process.

Any of the conventionally employed means of impregnating a porous solid with a soluble impregnating agent may be used. For example, the titanium halide may be dissolved in the hydrocarbon solvent and then added to or otherwise combined with the inorganic siliceous solids. The inorganic siliceous solids could also be added to the hydrocarbon solution of the titanium halide.

"Incipient wetness" impregnation techniques, whereby a minimum quantity of solvent is utilized in order to avoid formation of a slurry, are also suitable for use. The resulting mixture may be aged, optionally with agitation or other mixing, prior to further processing. Generally speaking, the impregnating solution should be placed in contact with the inorganic siliceous solids for a period of time sufficient for the solution to completely penetrate the available pore volume of the solids. The hydrocarbon solvent used for impregnation may thereafter be removed by drying at moderately elevated temperature (e.g., 50° C. to 200° C.) and/or reduced pressure (e.g., 1 mm Hg to 100 mm Hg) prior to calcination. The conditions in the solvent removal step are preferably selected so that at least 80%, more preferably at least 90%, of the hydrocarbon solvent used for impregnation is removed prior to calcination. The drying step may be preceded by decantation, filtration or centrifugation to remove any excess impregnation solution. Washing of the impregnated siliceous solid is not necessary. Thus, one desirable embodiment of this invention is characterized by the absence of such a washing step.

In another embodiment of the invention, the high surface area inorganic siliceous solid is impregnated by a vapor stream of titanium tetrachloride. The vapor stream is provided by flowing a gas over liquid titanium tetrachloride. The vaporization is conducted at temperatures greater than 50° C. at atmospheric pressure. Preferably, the vaporization temperature is greater than 80° C. and, most preferably, greater than 130° C. Alternatively, lower temperatures are possible by decreasing reaction pressure. Preferably, the gas is an inert gas such as nitrogen, helium, argon, carbon dioxide, and the like. The vapor stream of titanium tetrachloride is then passed over the high surface area inorganic siliceous solid to complete the impregnation step. The inorganic siliceous solid is maintained at a temperature greater than 50° C. during the impregnation. Preferably, the temperature of impregnation is maintained at greater than 80° C. and, most preferably, greater than 130° C.

Following impregnation, the vapor phase and liquid phase impregnated siliceous solids are calcined by firing at an elevated temperature. Calcination may be performed in the presence of oxygen (from air, for example) or, more preferably, an inert gas which is substantially free of oxygen such as nitrogen, argon, neon, helium or the like or mixture thereof. In one embodiment of the invention, calcination is first performed in a substantially oxygen-free atmosphere with oxygen being introduced thereafter. Preferably, the calcination atmosphere contains less than 10,000 ppm mole oxygen. More preferably, less than 2000 ppm mole oxygen is present in the calcination atmosphere. Ideally, the oxygen concentration during calcination is less than 500 ppm. It is recognized, however, that substantially oxygen-free conditions are difficult to attain in large-scale commercial operations. Optionally, the calcination may be performed in the presence of a reducing gas, such as carbon monoxide, when the some oxygen (e.g., up to 25,000 ppm mole) is present. The optimum amount of the reducing gas will, of course, vary depending upon a number of factors including the oxygen concentration in the calcination atmosphere and the identity of the reducing gas, but reducing gas levels of from 0.1 to 10 mole % in the calcination atmosphere are typically sufficient. In one embodiment of the invention, calcination is performed in an atmosphere comprised of oxygen, a reducing gas (preferably carbon monoxide) and, optionally, one or more inert gases (e.g., nitrogen, helium, argon, carbon dioxide).

The catalyst may be maintained in a fixed bed during calcination with a stream of gas being passed through the catalyst bed. To enhance the epoxidation activity of the catalyst, it is important that the calcination be performed at a temperature of at least 500° C. More preferably, the calcination temperature is at least 700° C. but no greater than 1000° C. Typically, calcination times of from about 0.1 to 24 hours will be sufficient.

The catalyst may be reacted with water after and/or during calcination. Such reaction can be effected by, for example, contacting the catalyst with steam at an elevated temperature (preferably, a temperature in excess of 100° C., more preferably, a temperature in the range of 150° C. to 650° C.) for from about 0.1 to 6 hours. Reaction with water is desirable in order to reduce the amount of residual halide in the catalyst derived from the titanium halide reagent and to increase the hydroxy density of the catalyst.

The catalyst may also be treated with an organic silylating agent at elevated temperature. Epoxide selectivity is generally improved by silylation. Silylation is preferably performed after calcination and most preferably after both calcination and reaction with water. Suitable silylation methods adaptable for use in the present invention are described in U.S. Pat. Nos. 3,829,392 and 3,923,843 (incorporated hereby by reference in their entirety). Suitable silylating agents include organosilanes, organohalosilanes, and organodisilazanes.

Organosilanes containing from one to three organic substituents may be utilized, including, for example, chlorotrimethylsilane, dichlorodimethyl silane, nitrotrimethyl-silane, chlorotriethylsilane, chlorodimethylphenylsilane and the like. Preferred organohalosilane silylating agents include tetra-substituted silanes having from 1 to 3 halo substituents selected from chlorine, bromine, and iodine with the remainder of the substituents being methyl, ethyl, phenyl or a combination thereof.

Organodisilazanes are represented by the formula $R_3Si-NH-SiR_3$, wherein the R groups are independently hydrocarbyl groups (preferably, $C_1-C_4$ alkyl) or hydrogen. Especially preferred for use are the hexaalkyl substituted disilazanes such as, for example, hexamethyldisilazane.

Treatment with the silylating agent may be performed either in the liquid phase (i.e., where the silylating agent is applied to the catalyst as a liquid, either by itself or as a solution in a suitable solvent such as a hydrocarbon) or in the vapor phase (i.e., where the silylating agent is contacted with the catalyst in the form of a gas). Treatment temperatures are preferably in the range of from about 80° C. to 450° C., with somewhat higher temperatures (e.g., 300° C. to 425° C.) being generally preferred wherein the silylating agent is an organohalosilane and somewhat lower temperatures (e.g., 80° C. to 300° C.) being preferred for the organodisilazanes. The silylation may be carried out in a batch, semi-continuous, or continuous manner.

The length of time required for the silylating agent to react with the surface of the catalyst depends in part on the temperature and agent employed. Lower temperatures generally require longer reaction times. Generally, times of from 0.1 to 48 hours are suitable.

The amount of silylating agent employed can vary widely. Suitable amounts of silylating agent can range from about 1 percent by weight (based on the weight of the entire catalyst composition) to about 75 percent by weight, with amounts of from 2 to 50 percent by weight typically being preferred. The silylating agent can be applied to the catalyst either in one treatment or a series of treatments.

The catalyst composition obtained by the aforedescribed procedure will generally have a composition comprising from about 0.1 to 15 percent (preferably, 1 to 10 percent) by weight titanium (in the form of titanium oxide, typically, and preferably, in a high positive oxidation state). Where the catalyst has been silylated, it will typically also contain 1 to 20 percent by weight carbon in the form of organic silyl groups. Relatively minor quantities of halide (e.g., up to about 5000 ppm) may also be present in the catalyst.

The catalyst compositions may optionally incorporate non-interfering and/or catalyst promoting substances, especially those which are chemically inert to the epoxidation reactants and products. The catalysts may contain minor amounts of promoters, for example, alkali metals (e.g., sodium, potassium) or alkaline earth metals (e.g., barium, calcium, magnesium) as oxides or hydroxides. Alkali metal and/or alkaline earth metal levels of from 0.01 to 5% by weight based on the total weight of the catalyst composition are typically suitable.

The catalyst compositions may be employed in any convenient physical form such as, for example, powder, flakes, granules, spheres or pellets. The inorganic siliceous solid may be in such form prior to impregnation and calcination or, alternatively, be converted after impregnation and/or calcination from one form to a different physical form by conventional techniques such as extrusion, pelletization, grinding or the like.

The epoxidation process of the invention comprises contacting an olefin with an organic hydroperoxide in the presence of the titanium catalyst. Suitable olefins include any olefin having at least one carbon-carbon double bond, and generally from 2 to 60 carbon atoms. Preferably the olefin is an acyclic alkene of from 3 to 10 carbon atoms such as propylene, butene, pentene, hexene, heptene, octene, nonene, decene, and isomers thereof. Also preferred are olefinically unsaturated compounds substituted with a hydroxyl group or a halogen group such as allyl chloride or allyl alcohol. Particularly preferred olefin is propylene.

Preferred organic hydroperoxides are hydrocarbon hydroperoxides having from 3 to 20 carbon atoms. Particularly preferred are secondary and tertiary hydroperoxides of from 3 to 15 carbon atoms, especially secondary alkyl hydroperoxides wherein the hydroperoxy group is on a carbon atom attached directly to an aromatic ring, e.g., ethylbenzene hydroperoxide. Other exemplary organic hydroperoxides suitable for use include t-butyl hydroperoxide, t-amyl hydroperoxide, cyclohexyl hydroperoxide, and cumene hydroperoxide.

In such an epoxidation process the olefin:hydroperoxide molar ratio is not particularly critical, but it is preferable to employ a molar ratio of from 1:1 up to 20:1.

The epoxidation reaction is conducted in the liquid phase in solvents or diluents that are liquid at the reaction temperature and pressure and are substantially inert to the reactants and the products produced therefrom. In commercial practice, it will generally be most economical to use as a solvent the hydrocarbon used to produce the organic hydroperoxide reactant. For example, when ethylbenzene hydroperoxide is utilized, the use of ethylbenzene as the epoxidation solvent is preferred. It is conducted at moderate temperatures and pressures. Typically, the organic hydroperoxide is present at concentrations of from about I to 50 percent by weight of the epoxidation reaction mixture (including olefin). Suitable reaction temperatures vary from 0° C. to 200° C., but preferably from 25° C. to 150° C. The reaction is preferably conducted at or above atmospheric pressure. The precise pressure is not critical. The reaction mixture may, for example, be maintained substantially in a non-gaseous phase or as a two phase (gas/liquid) system. The catalyst composition, of course, is heterogeneous in character and thus is present as a solid phase during the epoxidation process of this invention. Typical pressures vary from 1 atmosphere to 100 atmospheres.

The epoxidation may be performed using any of the conventional reactor configurations known in the art for reacting olefin and organic hydroperoxide in the presence of an insoluble catalyst. Continuous as well as batch procedures may be used. For example, the catalyst may be deployed in the form of a fixed bed or slurry with provisions being made for removal of heat generated as a result of the exothermic epoxidation reaction. A fixed bed catalytic reactor adaptable for use with the present process is described in EP 323,663. When the epoxidation has proceeded to the desired extent, the product mixture is separated and the products (epoxide and the alcohol derived from the organic hydroperoxide) recovered by conventional methods such as fractional distillation, selective extraction, filtration, and the like. The reaction solvent, the catalyst composition, and any unreacted olefin or organic hydroperoxide are recycled for further utilization.

The following examples merely illustrate the invention. Those skilled in the art will recognize many variations that are within the spirit of the invention and scope of the claims.

EXAMPLE 1: CATALYST PREPARATION IN ACCORDANCE WITH THE INVENTION

MCM-41 silica support can be made according to any known literature procedure. See, for example, U.S. Pat. No. 3,556,725, DiRenzo, et. al., *Microporous Materials* (1997), Vol. 10, 283, or Edler, et. al., *J. Chem. Soc., Chem. Comm.* (1995), 155. The obtained MCM-41 gel is calcined at 550° C. for 14 hours before use.

Catalyst 1A:

MCM-41 (4.36 g, BET surface area is 1488 $m^2/g$) is placed into a 500-mL 3-neck round-bottom flask equipped with an inert gas inlet, a gas outlet, and a scrubber containing aqueous sodium hydroxide solution. A titanium (IV) tetrachloride solution (0.55 mL, 0.95 g TiCl4 in 60 g n-heptane, 99+%, water <50 ppm) is added to the MCM-41 under dry inert gas atmosphere. The mixture is mixed well by swirling and the solvent is removed by roto-evaporation under vacuum at 80° C.

The above impregnated material is charged into a tubular quartz reactor (1 inch ID, 16 inch long) equipped with a thermowell, a 500 mL 3-neck round-bottom flask, a heating mantle, an inert gas inlet, and a scrubber (containing sodium hydroxide solution). The catalyst bed is heated at 850° C. under a 400 cc/min flow of dry nitrogen (99.999%) for 30 minutes before cooling to 400° C. Water (3.0 g) is then added into the 3-neck round-bottom flask and the flask is heated with a heating mantle to reflux under 400 cc/min flow of nitrogen to distill the water through the catalyst bed over a period of 30 minutes. A heat gun is used to heat the round-bottom flask to drive any residual water through the bed. The bed is then maintained at 400° C. for an additional 2 hours before cooling to room temperature.

The non-silylated Ti/MCM-41 catalyst (3.72 g) is added to a 500 mL 3-neck round-bottom flask equipped with a condenser, a thermometer, and an inert gas inlet. Hexamethyldisilazane (0.96 g) in heptane (36 g, water <50 ppm) is added to the Ti/MCM-41 and the system is heated in an oil bath (115° C.) to reflux (98° C.) under inert atmosphere for 2 hours before cooling to room temperature. The catalyst is filtered and then dried under inert gas flow at 180° C. for 1.5 hours. Measured Ti loading of the catalyst is 5.0 wt %.

Catalyst 1B:

MCM-41 silica (4.0 g, BET surface area is 1140 $m^2/g$) is charged into a tubular quartz reactor (1 inch ID, 16 inch long) equipped with a thermowell, a 500 mL 3-neck round-bottom flask, a heating mantle, an inert gas inlet, and a scrubber (containing sodium hydroxide solution). The catalyst bed is heated to 400° C. under dry nitrogen (99.999%) flow (400 cc/min). Water (1.0 g) is then added into the 3-neck round-bottom flask and the flask is heated with a heating mantle to reflux under 400 cc/min flow of nitrogen to distill the water through the catalyst bed over a period of 30 minutes. A heat gun is used to heat the round-bottom flask to drive any residual water through the bed. The bed is then cooled to 300° C.

Titanium tetrachloride (3.29 g) is transferred to the 3-neck round-bottom flask and the flask is heated with a heating mantle reflux under 400 cc/min flow of nitrogen to distill the $TiCl_4$ through the catalyst bed over a period of 1 hour. A heat gun is used to heat the round-bottom flask to drive any residual $TiCl_4$ through the bed. The bed is then heated at 700° C. for 0.5 hour before cooling to 400° C. Water (1.0 g) is then added into the 3-neck round-bottom flask and the flask is heated with a heating mantle to reflux under 400 cc/min flow of nitrogen to distill the water through the catalyst bed over a period of 30 minutes. A heat gun is used to heat the round-bottom flask to drive any residual water through the bed before cooling to room temperature.

Silylation of the nonsilylated Ti/MCM-41 catalyst is performed according the procedure of Catalyst 1A. Measured Ti loading of the catalyst is 4.9 wt %.

COMPARATIVE EXAMPLE 2: CATALYST PREPARATION ACCORDING TO WO 98/50374

Comparative Catalyst 2A:

Silica support (Grace Davison DAVICAT P-732, particle size 0.6–1.4 mm, surface area 300 $m^2/g$) is dried at 500° C. in air for 2 hours before cooling to room temperature. The dried silica (162 g) is placed into a 500-mL 3-neck round-bottom flask equipped with an inert gas inlet, a gas outlet, and a scrubber containing aqueous sodium hydroxide solution. A titanium (IV) tetrachloride solution (11.75 mL, 20.32 g $TiCl_4$ in 252 g n-heptane, 99+%, water <50 ppm) is added to the silica under dry inert gas atmosphere. The mixture is mixed well by swirling and the solvent is removed by roto-evaporation under vacuum at 80° C.

A portion (35 g) of the above impregnated material is charged into a tubular quartz reactor (1 inch ID, 16 inch long) equipped with a thermowell, a 500 ml 3-neck round-bottom flask, a heating mantle, an inert gas inlet, and a scrubber (containing sodium hydroxide solution). The catalyst bed is heated at,850° C. under a 400 cc/min flow of dry nitrogen (99.999%) for 30 minutes before cooling to 400° C. Water (3.0 g) is then added into the 3-neck round-bottom flask and the flask is heated with a heating mantle to reflux under 400 cc/min flow of nitrogen to distill the water through the catalyst bed over a period of 30 minutes. A heat gun is used to heat the round-bottom flask to drive any residual water through the bed. The bed is then maintained at 400° C. for an additional 2 hours before cooling to room temperature.

The nonsilylated Ti/silica catalyst is added to a 500 mL 3-neck round-bottom flask equipped with a condenser, a thermometer, and an inert gas inlet. Hexamethyldisilazane (6.0 g) in heptane (76 g, water <50 ppm) is added to the Ti/silica and the system is heated in an oil bath (115° C.) to reflux (98° C.) under inert atmosphere for 2 hours before cooling to room temperature. The catalyst is filtered, washed with 100 mL heptane, and then dried under inert gas flow at 180°–200° C. for 2 hours. Measured Ti loading of the catalyst is 2.97 wt %.

Comparative Catalyst 2B:

Silica support (Grace Davison DAVICAT P-732, particle size 0.6–1.4 mm, surface area 300 $m^2/g$) is dried at 400° C. in air for 4 hours before cooling to room temperature. The dried silica (177 g) is placed into a 500-mL 3-neck round-bottom flask equipped with an inert gas inlet, a gas outlet, and a scrubber containing aqueous sodium hydroxide solution. A titanium (IV) tetrachloride solution (19 mL, 32.87 g $TiCl_4$ in 262 g n-heptane, 99+%, water <50 ppm) is added to the silica under dry inert gas atmosphere. The mixture is mixed well by swirling and the solvent is removed by roto-evaporation under vacuum at 80° C.

The rest of the procedure is the same as the Catalyst 3 preparation. Measured Ti loading of the catalyst is 3.2 wt %.

Comparative Catalyst 2C:

Silica support (Grace Davison DAVICAT P-732, particle size 0.6–1.4 mm, surface area 300 $m^2/g$) is dried at 300° C. in air for 4 hours before cooling to room temperature. The dried silica (168 g) is placed into a 500-mL 3-neck round-bottom flask equipped with an inert gas inlet, a gas outlet, and a scrubber containing aqueous sodium hydroxide solution. A titanium (IV) tetrachloride solution (18.2 mL, 31.5 g $TiCl_4$ in 252 g n-heptane, 99+%, water <50 ppm) is added to the silica under dry inert gas atmosphere. The mixture is mixed well by swirling and the solvent is removed by roto-evaporation under vacuum at 80° C.

The rest of the procedure is the same as the Catalyst 3 preparation. Measured Ti loading of the catalyst is 4.2 wt %.

COMPARATIVE EXAMPLE 3: CATALYST PREPARATION ACCORDING TO EP 345,856

Comparative Catalyst 3A:

Silica support (Grace Davison DAVICAT P-732, particle size 0.6–1.4 mm, surface area 300 $m^{2/}g$) is dried at 450° C. in air for 2 hours before cooling to room temperature. The dried silica (37 g) is placed into a tubular quartz reactor (1 inch ID, 16 inch long) equipped with a thermowell, a 500 mL 3-neck round-bottom flask, a heating mantle, an inert gas inlet, and a scrubber (containing sodium hydroxide solution). The catalyst bed is heated to 200° C. under dry nitrogen (99.999%) flow (400 cc/min). Titanium tetrachloride (19 g) is then added into the 3-neck round-bottom flask and the flask is heated with a heating mantle to reflux under 400 cc/min flow of nitrogen to distill the $TiCl_4$ through the catalyst bed over a period of 1 hour. A heat gun is used to heat the round-bottom flask to drive any residual $TiCl_4$ through the bed. The bed is then heated to 600° C. and maintained at 600° C. for 2 hours before cooling to 300° C.

Water (3.0 g) is then added into the 3-neck round-bottom flask and the flask is heated with a heating mantle to reflux under 400 cc/min flow of nitrogen to distill the water through the catalyst bed over a period of 30 minutes. A heat gun is used to heat the round-bottom flask to drive any residual water through the bed before cooling to 200° C. Hexamethyldisilazane (4.0 g) is then added into the 3-neck round-bottom flask and the flask is heated with a heating mantle to reflux under 400 cc/min flow of nitrogen to distill the hexamethyldisilazane through the catalyst bed over a period of 1 hour. A heat gun is used to heat the round-bottom flask to drive any residual hexamethyldisilazane through the bed before cooling to room temperature. Catalyst contained 3.0 wt % Ti.

Comparative Catalyst 3B

Silica support (Grace Davison DAVICAT P-732, particle size 0.6–1.4 mm, surface area 300 $m^2/g$) is dried at 450° C. in air for 2 hours before cooling to room temperature. The dried silica (36 g) is placed into a tubular quartz reactor (1 inch ID, 16 inch long) equipped with a thermowell, a 500 mL 3-neck round-bottom flask, a heating mantle, an inert gas inlet, and a scrubber (containing sodium hydroxide solution). The catalyst bed is heated to 300° C. under dry nitrogen (99.999%) flow (400 cc/min). Titanium tetrachloride (7.4 g) is then added into the 3-neck round-bottom flask and the flask is heated with a heating mantle to reflux under 400 cc/min flow of nitrogen to distill the $TiCl_4$ through the catalyst bed over a period of 1 hour. A heat gun is used to heat the round-bottom flask to drive any residual $TiCl_4$ through the bed. The bed is then heated to 850° C. and maintained at 850° C. for 0.5 hour before cooling to 400° C.

Water (3.0 g) is then added into the 3-neck round-bottom flask and the flask is heated with a heating mantle to reflux under 400 cc/min flow of nitrogen to distill the water through the catalyst bed over a period of 30 minutes. A heat gun is used to heat the round-bottom flask to drive any residual water through the bed before cooling to room temperature.

The nonsilylated Ti/silica catalyst (15 g) is added to a 500 mL 3-neck round-bottom flask equipped with a condenser, a thermometer, and an inert gas inlet. Hexamethyldisilazane (3.0 g) in heptane (43 g, water <50 ppm) is added to the Ti/silica and the system is heated in an oil bath (115° C.) to reflux (98° C.) under inert atmosphere for 2 hours before cooling to room temperature. The catalyst is filtered and then dried under inert gas flow at 180° C. for 1 hour. Measured Ti loading of the catalyst is 2.6 wt %.

COMPARATIVE EXAMPLE 4: CATALYST PREPARATION USING TITANIUM ISOPROPOXIDE PRECURSOR AND MCM-41 SUPPORT

Comparative Catalyst 4A:

The MCM-41 gel is pyrolyzed at 550° C. under nitrogen flow and then calcined in air for 14 hours at 550° C. BET surface area of the material is 1100 $m^2/g$. MCM-41 (2.42 g) is placed into a 500-mL 3-neck round-bottom flask equipped with an inert gas inlet and a gas outlet. A titanium (IV) diisopropoxide bis(acetylacetonate) solution (0.74 g of 75% Ti($^i$OPr)$_2$(acac)$_2$ in 39.7 g anhydrous isopropanol) is added to the MCM-41 under dry inert gas atmosphere. The slurry is mixed well and the solvent is removed by nitrogen stripping at 100° C. The catalyst is calcined at 800° C. in air for 2 hours.

The nonsilylated Ti/silica catalyst is added to a 500 mL 3-neck round-bottom flask equipped with a condenser, a thermometer, and an inert gas inlet. Hexamethyldisilazane (1.5 g) in heptane (43 g, water <50 ppm) is added to the Ti/silica and the system is heated in an oil bath (115° C.) to reflux (98° C.) under inert atmosphere for 2 hours before cooling to room temperature. The catalyst is filtered and then dried under inert gas flow at 180° C. for 1 hour. Measured Ti loading of the catalyst is 2.6 wt %.

Comparative Catalyst 4B:

The MCM-41 gel is pyrolyzed at 550° C. under nitrogen flow and then calcined in air for 14 hours at 550° C. BET surface area of the material is 1100 m$^2$/g. MCM-41 (2.42 g) is placed into a 500-mL 3-neck round-bottom flask equipped with an inert gas inlet and a gas outlet. A titanium (IV) diisopropoxide bis(acetylacetonate) solution (1.22 g of 75% Ti($^i$OPr)$_2$(acac)$_2$ in isopropanol, in 39.5 g anhydrous isopropanol) is added to the MCM-41 under dry inert gas atmosphere. The slurry is mixed well and the solvent is removed by nitrogen stripping at 100° C. The catalyst is calcined at 800° C. in air for 2 hours.

Silylation of the nonsilylated Ti/MCM-41 catalyst is performed according the procedure of Comparative Catalyst 4A. Measured Ti loading of the catalyst is 4.0 wt %.

COMPARATIVE EXAMPLE 5: CATALYST PREPARATION ACCORDING TO MASCHMEYER, ET. AL.

Comparative Catalyst 5:

This example demonstrates, for comparative purposes, the preparation of a catalyst from a titanocene dichloride precursor according to the procedures of Maschmeyer, et. al., *Nature* (1995) V. 378, 159.

Titanocene dichloride (3.15 g) is weighed into a 250 ml flask and 142 g dry dichloromethane (Aldrich, anhydrous) is added. The flask is swirled vigorously. MCM-41 silica support (surface area 1252 m$^2$/g) is then added to the above mixture and the mixture is stirred for 30 minutes. Triethylamine (5.12 g) is added to the mixture and stirred for an additional 2 hours. The reaction mixture is filtered and the filter cake is washed with dichloromethane (3×80 ml).

The solid is packed into tube reactor (1 inch ID) equipped with a thermowell, a 500 ml 3-neck round-bottom flask, a heating mantle, an inert gas inlet, and a scrubber. The catalyst bed is heated to 20° C. under dry nitrogen (99.999%) flow (400 cc/min) and the material dried for 1 hour. Then the catalyst bed is heated to 550° C. under air flow (400 cc/min) and it calcined under air flow for 2 hour.

Silylation of the nonsilylated Ti/MCM-41 catalyst is performed according the procedure of Comparative Catalyst 4A. Measured Ti loading of the catalyst is 8.5 wt %.

EXAMPLE 6: BATCH EPOXIDATION OF 1-OCTENE WITH EBHP OXIDATE AT 50° C.

To evaluate the performance of the catalysts prepared in Example 1 and Comparative Examples 2–5, batch epoxidations of 1-octene using ethylbenzene hydroperoxide were carried out. The following procedure is employed.

A feed solution is prepared by mixing 220 g 1-octene, 50 g EBHP oxidate, and 10 g nonane (internal standard). A portion of the feed solution (28 g) is transferred under inert atmosphere to a 4-neck 100 mL round bottom flask attached to a condenser, a thermocouple, a stirrer bar, and a sampling port. The mixture is heated to 50° C., while stirring (with a stir bar) at a rate of 700 rpm. A Ti/silica or Ti/MCM-41 catalyst (powder, 0.2 g) is then added to the flask and the mixture is heated for 30 minutes at 50° C. A product sample (3 mL) is taken 30 minutes after catalyst addition. Both the feed sample and the product sample are analyzed by GC for EBHP and epoxyoctane concentrations. Conversion and epoxide selectivity are calculated relative to hydroperoxide consumed. First order activity (k) is calculated by the equation k=-[ln(1- % conversion)].

These results, in Table 1, show that the use of high surface area supports leads to an unexpected increase in activity of 2–4 times previous catalyst preparations on silica (WO 98/50374 or EP 345,856) or MCM-41 (Maschmeyer, et. al.). Also, liquid phase and vapor phase impregnation of MCM-41 result in equivalent catalyst activity.

TABLE 1

COMPARISON OF CATALYST ACTIVITY

| Catalyst | Support Surface Area (m$^2$/g) | Preparation Method | Support | Ti loading (wt. %) | EBHP Conversion (%) | k |
|---|---|---|---|---|---|---|
| 1A | 1488 | TiCl$_4$ in heptane | MCM-41 | 5.0 | 77 | 1.47 |
| 1B | 1140 | TiCl$_4$ - vapor phase addition | MCM-41 | 4.9 | 77 | 1.47 |
| 2A* | 300 | TiCl$_4$ in heptane | Silica | 3.0 | 51.5 | 0.72 |
| 2B* | 300 | TiCl$_4$ in heptane | Silica | 3.2 | 49 | 0.67 |
| 2C* | 300 | TiCl$_4$ in heptane | Silica | 4.2 | 51 | 0.71 |
| 3A* | 300 | TiCl$_4$ - vapor phase addition | Silica | 3.0 | 48 | 0.65 |
| 3B* | 300 | TiCl$_4$ - vapor phase addition | Silica | 2.6 | 48 | 0.65 |
| 4A* | 1100 | Ti($^i$OPr)$_2$(acac)$_2$ | MCM-41 | 2.6 | 32 | 0.38 |
| 4B* | 1100 | Ti($^i$OPr)$_2$(acac)$_2$ | MCM-41 | 4.0 | 33 | 0.40 |
| 5* | 1252 | Cp$_2$TiCl$_2$ | MCM-41 | 8.5 | 42 | 0.54 |

*Comparative Example

We claim:

1. An epoxidation process comprising contacting an organic hydroperoxide with an olefin in the presence of a catalyst obtained by a method comprising the steps of:
    (a) impregnating an inorganic siliceous solid with a titanium source selected from the group consisting of:
        (1) a solution of a titanium halide in a non-oxygenated hydrocarbon solvent; and
        (2) a vapor stream of titanium tetrachloride; said inorganic siliceous solid having a surface area greater than 1100 m$^2$/g;
    (b) calcining the impregnated siliceous solid to form the catalyst composition; and
    (c) optionally, heating the catalyst in the presence of water;
    said method being characterized by the substantial exclusion of water until at least after step (a) is completed.

2. The epoxidation process of claim 1 wherein the titanium halide is titanium tetrachloride.

3. The epoxidation process of claim 1 wherein impregnation step (a)(1) is accomplished by combining a solution of the titanium halide in the non-oxygenated hydrocarbon solvent with the inorganic siliceous solid and thereafter removing the hydrocarbon solvent.

4. The epoxidation process of claim 1 wherein the inorganic siliceous solid is MCM-41.

5. The epoxidation process of claim 1 wherein the non-oxygenated hydrocarbon solvent is selected from the group consisting of $C_5$–$C_{12}$ aliphatic hydrocarbons, $C_6$–$C_{12}$ aromatic hydrocarbons, $C_1$–$C_{10}$ halogenated aliphatic hydrocarbons, $C_6$–$C_{10}$ halogenated aromatic hydrocarbons, and mixtures thereof.

6. The epoxidation process of claim 1 wherein water is substantially excluded until after step (b) is completed.

7. The epoxidation process of claim 1 wherein the method of obtaining the catalyst comprises an additional step after step (c) of treating the catalyst with a silylating agent.

8. The epoxidation process of claim 7 wherein the silylating agent is selected from the group consisting of organosilanes, organohalosilanes, organodisilazanes, and mixtures thereof.

9. The epoxidation process of claim 1 wherein calcination step (b) is performed at a temperature of at least 500° C.

10. The epoxidation process of claim 1 wherein the organic hydroperoxide is ethylbenzene hydroperoxide or t-butyl hydroperoxide.

11. The epoxidation process of claim 1 wherein the olefin is a $C_3$–$C_{10}$ acyclic alkene.

12. The epoxidation process of claim 1 wherein step (b) is performed in a substantially oxygen-free atmosphere.

13. The epoxidation process of claim 1 wherein step (b) is performed in an atmosphere comprised of oxygen and a reducing gas.

* * * * *